United States Patent
Adage

(10) Patent No.: US 11,413,247 B2
(45) Date of Patent: Aug. 16, 2022

(54) BATCH-WISE MELT EXTRUSION PROCESS AND DEVICE FOR PREPARING A SOLID DISPERSION

(71) Applicant: BIT Pharma GmbH, Graz (AT)

(72) Inventor: Tiziana Adage, Graz (AT)

(73) Assignee: BIT PHARMA GMBH

( * ) Notice: Subject to any disclaimer, the term of this patent is extended or adjusted under 35 U.S.C. 154(b) by 57 days.

(21) Appl. No.: 16/767,032

(22) PCT Filed: Nov. 29, 2018

(86) PCT No.: PCT/EP2018/083009
§ 371 (c)(1),
(2) Date: May 26, 2020

(87) PCT Pub. No.: WO2019/106090
PCT Pub. Date: Jun. 6, 2019

(65) Prior Publication Data
US 2020/0368165 A1    Nov. 26, 2020

(30) Foreign Application Priority Data
Nov. 30, 2017 (EP) .................... 17204645

(51) Int. Cl.
| | | |
|---|---|---|
| *A61K 9/20* | (2006.01) | |
| *A61K 31/4422* | (2006.01) | |
| *B29C 48/00* | (2019.01) | |
| *B29K 67/00* | (2006.01) | |
| *B29K 105/00* | (2006.01) | |

(52) U.S. Cl.
CPC .......... *A61K 9/204* (2013.01); *A61K 31/4422* (2013.01); *B29C 48/022* (2019.02); *B29K 2067/043* (2013.01); *B29K 2067/046* (2013.01); *B29K 2105/0035* (2013.01)

(58) Field of Classification Search
CPC .... A61K 9/204; A61K 9/1694; A61K 9/1647; A61K 9/1682; A61K 31/4422; B29C 48/022; B29K 2067/043; B29K 2067/046; B29K 2105/0035
See application file for complete search history.

(56) References Cited

U.S. PATENT DOCUMENTS 5,792,474 A * 8/1998 Rauchfuss ........... A61K 9/1617
424/449
6,318,650 B1    11/2001 Breitenbach et al.
2004/0173923 A1    9/2004 Schutz et al.

FOREIGN PATENT DOCUMENTS

| EP | 0043254 A1 | 1/1982 |
| EP | 2308478 A1 | 4/2011 |
| WO | 2002094226 A1 | 11/2002 |

OTHER PUBLICATIONS

Patent Cooperation Treaty, International Searching Authority, Search Report and Written Opinion for PCT/EP2018/083009, 8 pages, dated Feb. 12, 2019.

* cited by examiner

*Primary Examiner* — Carlos A Azpuru
(74) *Attorney, Agent, or Firm* — Viksnins Harris Padys Malen LLP

(57) ABSTRACT

The present invention relates to a melt extrusion process for preparing a solid dispersion comprising a pharmaceutically active ingredient, a polymeric binder, and, optionally, one or more auxiliary agents, comprising a) in a batch-wise operation, placing a pre-determined amount of the polymeric binder, a pre-determined amount of the active ingredient, and, optionally, a pre-determined amount of the auxiliary agent(s) in a melting vessel; melting the polymeric binder with agitation to disperse the active ingredient in the polymeric binder to obtain a molten pre-dispersion; b) feeding the pre-dispersion into an extruder to homogenize the pre-dispersion and release a melt through a die; and c) allowing the melt to solidify.

13 Claims, No Drawings

BATCH-WISE MELT EXTRUSION PROCESS AND DEVICE FOR PREPARING A SOLID DISPERSION

CROSS-REFERENCE TO RELATED APPLICATION(S)

This application claims the benefit of priority of EP Application No. 17204645.0, filed Nov. 30, 2017.

The present invention relates to a melt extrusion process and device for preparing a solid dispersion comprising a pharmaceutically active ingredient, a polymeric binder, and, optionally, one or more auxiliary agents.

In general terms, the process of melt extrusion is carried out in the conventional extruders as known to a person skilled in the art.

The melt extrusion process comprises the steps of preparing a melt of one or more pharmaceutically active ingredients, the polymeric binder and the auxiliary agents, and cooling the melt until it solidifies. "Melting" means a transition into a liquid or rubbery state in which it is possible for one component to get embedded homogeneously in the other. Further, melt extrusion is a fast, continuous, manufacturing process without requirement of further drying or discontinuous process steps. It provides short thermal exposure and therefore allows processing of heat sensitive active ingredients. Process temperatures can be reduced by addition of plasticizers. It requires comparatively lower investment for equipment as against other processes.

According to the conventional procedure, such as the procedure described in U.S. Pat. No. 5,792,4474, the one or more pharmaceutically active ingredients, polymeric binders, and, optionally, auxiliary agents are dry-mixed to obtain a powder blend which is transferred to an extruder. Rotating screws of the extruder move the blend through the heated barrel of an extruder whereby the powder blend melts and molten dispersion product is released through a die. It is then allowed to cool to form an extrudate. Agitation of the powder blend that occurs during processing contributes to the homogeneity of the extrudate. Shaping of the extrudate can conveniently be carried out using a calender with two counter-rotating rollers with mutually matching depressions on their surface. A broad range of tablet forms can be attained by using rollers with different forms of depressions. Alternatively, the extrudate is cut into pieces before, while or after solidification. It can be processed further into suitable pharmaceutical dosage forms.

However, the particles of active ingredient tend to aggregate before extrusion due to high surface energy even though they have been dry-blended with polymeric binders and optionally auxiliary agents. Also, due to different specific weights and different intake behavior of the components in the extruder hopper, the powder blend may separate before the blend melts. This may result in an inhomogeneous distribution of the drug within the solid dispersion and uniformity of content of the dosage forms is difficult to attain.

The problems are aggravated when the solid dispersion recipe contains components which are semi-solid, tacky and/or viscous at ambient temperature such as plasticizers or low-melting binders. It is virtually impossible to evenly distribute such components in the melt during extrusion. For this reason, a granulation step is usually employed in which the plasticizer is granulated with one or all of the other solid components of the formulation prior to extrusion. However, the granulation step adds to the complexity of the process.

Further, very tacky or viscous components are difficult to handle and are difficult to granulate with the solid components.

WO 02/094226 describes a method for the solvent-free production of a homogenized product, especially for implants or microparticles, whereby at least one polymer and at least one active ingredient in the form of raw materials are homogenized at or below the glass transition temperature of the polymer(s), especially at cryogenic temperatures. Cooling to a temperature applied in cryogenic technology can be carried out, especially to the temperature of dry ice or of a liquid gas, especially to the temperature of liquid nitrogen.

The present invention seeks to provide a process for preparing a solid dispersion of a pharmaceutically active ingredient that allows for high uniformity of content at minimum effort, e.g., without adding significantly to the investment for equipment, in particular in such cases where the solid dispersion recipe contains semi-solid, tacky and/or viscous components.

This is achieved by a melt extrusion process for preparing a solid dispersion comprising a pharmaceutically active ingredient, a polymeric binder, and, optionally, one or more auxiliary agents, comprising a) in a batch-wise operation, placing a pre-determined amount of the polymeric binder, a pre-determined amount of the active ingredient, and, optionally, a pre-determined amount of the auxiliary agent(s) in a melting vessel; melting the polymeric binder with agitation to disperse the active ingredient in the polymeric binder to obtain a molten pre-dispersion;

b) feeding the pre-dispersion into an extruder to homogenize the pre-dispersion and release a melt through a die; and c) allowing the melt to solidify.

According to the process of the invention, high uniformity of content is reached at minimum effort. Pre-dispersing in step a) is carried out in the presence of molten polymeric binder. This simplifies mixing of polymeric binder, active ingredient and, optionally, auxiliary agent(s). Step a) thus provides a more uniform pre-dispersion at less effort than prior art processes where the mix to be fed into the extruder is a powder-blend made by comminution of solids. Typically, in the pre-dispersion, the components are intermixed in a liquid or viscous state and the components are at least partially dissolved in one another. This minimizes the risk of separation of components in the downstream extrusion step.

Partial homogenization is achieved by melting the polymeric binder with agitation in step a). As a consequence, the process according to the invention needs less stringent conditions in the subsequent extrusion whereas in prior art processes homogenization is effected almost exclusively in the extrusion step. As high uniformity is reached already in step a), no or only little further homogenization has to be achieved in the extruder. In the extruder, thermal and mechanical energy input can be kept at a minimum, i.e. just sufficient for melting and for establishing sufficient pressure for releasing the melt through the die.

According to the invention, pre-determined amounts of different components, i.e., of the polymeric binder and the pharmaceutically active ingredient and, optionally of the auxiliary agent(s), are placed in a melting vessel. The pre-determined amounts are determined by any suitable method known to those skilled in the art, for example, by weighing or measuring the volume of each of the components that are placed into the melting vessel. Components that are solid or semi-solid at room temperature are preferably weighed, whereas components that are liquid at room temperature are preferably placed into the melting vessel in pre-determined volumes. The term "melting vessel" comprises any kind of vessel, in particular, closable vessel, e.g., any vessel which allows for carrying out the different measures described in step a), in particular any vessel which comprises at least one opening for placing the components into the vessel. The vessel is designed such that the components in the vessel can be melted, e.g., heated, and agitated, e.g., stirred. The vessel is, for example, a beaker, in particular a pot, such as a stainless steel pot.

According to the invention, in the melting vessel, the polymeric binder is melted with agitation to disperse the active ingredient in the polymeric binder to obtain the molten pre-dispersion.

Melting of the polymeric binder typically involves heating of the content of the melting vessel by any means known to those skilled in the art for heating the content of vessels, in particular by any heating operation known to those skilled in the art for heating pharmaceutical compositions, i.e. where uniformity of thermal history is important and death volumes shall be avoided. The heat is, for example, delivered via the melting vessel itself, e.g., through the bottom and/or the side walls of the melting vessel. The heat may alternatively be delivered via heating devices that are introduced into the melting vessel, e.g. through an opening or openings of the melting vessel, and arranged such that a heating surface of the heating device is in contact with the content of the melting vessel.

The term "agitation" comprises any operation which ensures thorough mixing of the content of the melting vessel. Agitation may comprise moving the melting vessel itself. The movement of the melting vessel may comprise a rotating motion or shaking. The melting vessel itself may alternatively be static. Agitation may comprise stirring of the content of the melting vessel for example, with a mechanical stirrer.

It has surprisingly been found that ultrasonic treatment of the pre-dispersion can increase the efficiency of the process of the invention. An ultrasonic treatment is preferably carried out while dispersing the active ingredient in the polymeric binder and/or after dispersing the active ingredient in the polymeric binder. It is possible to carry out an ultrasonic treatment also in step b). Preferably, ultrasonic treatment is discontinued, when the pre-dispersion is fed into the extruder.

Systematic analysis of the solidified melt revealed that gas bubbles were present in those parts of the solidified melt which did not meet the specifications with regard to homogeneity. Gas bubbles may lead to uncontrolled release of (part of the) active ingredient from solid dispersions and are thus undesired. Preferably, only those parts of the solidified melt that are bubble-free are used in the treatment of patients and discarding those parts of the solidified melt which contain gas bubbles may limit process efficiency. It is assumed that gas is introduced from the surrounding atmosphere (typically air) when the polymeric binder is melted with agitation. The gas seems to accumulate in the agitated contents of the melting vessel. A high gas content of the pre-dispersion increases the risk of formation of gas bubbles in the melt when processed in the extruder, in particular when the melt is processed at increased temperature. Ultrasound, on the other hand, seems to accelerate the release of gas from the contents of the melting vessel and therefore reduces the amount of gas delivered into the extruder. This results in an essentially bubble-free solidified melt.

A person skilled in the art is familiar with ultrasonic treatment and the required equipment.

When the melting temperature of the polymeric binder is low, agitation (and the optional ultrasonic treatment) may produce sufficient heat to melt the polymeric binder without active heating of the contents of the melting vessel.

The molten pre-dispersion typically contains at least two phases. A first phase is a solution comprising molten polymeric binder. The solution comprises part of the active ingredient in dissolved form. If auxiliary agent(s) is/are present, the solution may further comprise auxiliary agent(s) in dissolved form. Further solid phase(s) are usually present in the form of dispersed particles. These solid phase(s) comprise active ingredient and, optionally, auxiliary agent (s) which was/were not fully dissolved by the molten polymeric binder.

Alternatively, the molten pre-dispersion may be a solution, i.e. monophasic. A monophasic solution is obtained when the active ingredient and optionally also the auxiliary agent(s) are dissolved completely by the polymeric binder. Typically, the solubility of the active ingredient and of auxiliary agent(s) in the polymeric binder increases with the temperature. Thus, when melting the polymeric binder with agitation, depending on the solubility of active ingredient(s) and auxiliary agent(s), it may be possible to increase the temperature such that the active ingredient and, if present, also the auxiliary agent(s) dissolve quantitatively in the polymeric binder. The person skilled in the art can easily determine a temperature at which the pre-dispersion becomes monophasic, i.e. when remaining solid or coexisting liquid phases disappear while the temperature increases very slowly.

According to the invention, the pre-dispersion is fed into an extruder. It is generally preferred to feed the molten pre-dispersion into the extruder, i.e. without allowing the pre-dispersion to solidify before it is fed into the extruder. Preferably, the temperature of the pre-dispersion while being fed into the extruder is above its solidification temperature.

The molten pre-dispersion can be fed into an extruder in various ways.

According to a preferred process of the invention, feeding the pre-dispersion into the extruder involves a displacement of the pre-dispersion from the melting vessel through an opening of the melting vessel, the displacement of the pre-dispersion being enforced by reducing a volume of the melting vessel being accessible for the pre-dispersion. The volume of the melting vessel being accessible for the pre-dispersion is reduced, for example, by a translational movement of a displacement element, e.g., a punch, into the melting vessel. The opening is preferably closable. The opening can be located in the bottom of the melting vessel. The translational movement of the punch is preferably a movement towards the bottom of the melting vessel and the pre-dispersion is displaced through the opening when the movement of the punch reduces a volume of the melting vessel between the punch and the bottom of the melting vessel.

The pre-dispersion fed into the extruder according to the invention has a higher degree of homogeneity than those mechanically homogenized products (as described, for example, in WO 02/094226) that are typically fed into the extruder according to the prior art, as pointed out above. As a consequence, more extrudate can be produced with a given extruder, or, a smaller extruder can be used for producing a pre-determined amount of extrudate, or, even higher homogeneity of the product is reached when extrusion is carried out as described in the prior art. When the molten pre-dispersion is a highly viscous solution, the purpose of extrusion is a compensation of remaining unequal distribution of the different components in the highly viscous solution and an adjustment of the desired temperature, i.e. desired viscosity for release through the die.

Alternatively, the molten pre-dispersion is allowed to solidify before it is fed into the extruder.

Conveniently, the molten pre-dispersion is portioned before it is allowed to solidify such that a solid particulate of pre-dispersion is obtained. Portioning may involve pouring of molten pre-dispersion into depressions of a casting mold in which the pre-dispersion is allowed to solidify. The casting mold and/or the immersions may be elastic, e.g., made of a silicone comprising material, to facilitate demolding of the solidified pre-dispersion. Alternatively, the molten pre-dispersion may be passed through calendar rolls having depressions on their surface. The particulate of pre-dispersion is then fed into the extruder, optionally after comminution.

The solidified pre-dispersion or pieces of solidified pre-dispersion may be comminuted and the comminuted solid pre-dispersion (which is in the form of solid particles) is fed into the extruder. Comminution includes every way of reducing the size of the solidified pre-dispersion into particles or pieces of defined or undefined shape which are small enough for feeding them into an extruder; e.g. breaking and/or cutting the partially or fully solidified mixture into such particles or pieces. Every method for reducing the particle size of solid ingredients of pharmaceutical dosage forms is suitable for comminuting the solidified pre-dispersion.

According to the invention, the pre-dispersion is homogenized during its passage through the extruder. Homogenized as used herein refers to bringing the pre-dispersion in a more homogeneous state. The melt released through the die has a higher degree of homogeneity than the pre-dispersion fed into the extruder. A higher degree of homogeneity is characterized, for example, by an increase of the relative amount of dissolved active ingredient(s); and/or by a decrease of the average particle size of dispersed solid particles. In one embodiment, the melt is homogeneous throughout and consists of only one phase thermodynamically.

Extrusion may, for example, comprise increasing the temperature of the pre-dispersion to a first target temperature and maintaining this first target temperature, decreasing the temperature to a second target temperature and maintaining the second target temperature before the melt is released through the die.

After reaching the first target temperature, this temperature is maintained for a period sufficiently long to ensure a complete melting of all components and their complete mixing in order to provide a homogeneous melt with no or essentially no temperature gradient throughout the molten mass. Depending on the total mass of components, the time period may range from 2 min to 30 min, such as 3 min to 25 min, 4 min to 20, or 5 min to 15 min. Preferably the time period is as short as possible in order to avoid thermal damage of the components of the melt. A suitable time period may be determined easily by those skilled in the art.

The second target temperature is chosen in order to establish a viscosity suitable for release of the melt through the die. The second target temperature for release is chosen to allow subsequent smooth extrusion by still providing a homogenous melt, sufficient viscosity for passage through an extrusion die at a chosen die pressure, form stability of the extruded mass and suitable solidification times thereof. The temperature reduction should be sufficiently slow to avoid local undercooling and concomitant risk of crystallization or precipitation of one or more components of the melt. Depending on the heat capacity of the melt components and the total mass thereof, the time period for cooling down the melt from the first target temperature to the second target temperature may range from 3 min to 60 min, in particular 4 min to 30 min, 5 min to 20 min, such as 5 min to 10 min. In order to avoid concentration or temperature gradient, the melt is preferably continuously mixed during temperature reduction.

After reaching the second target temperature, the temperature is kept constant for a period of time sufficiently long to ensure the equalization of a uniform or essentially uniform target temperature for release throughout the melt. Depending on the total mass of the melt and the components contained therein, the period of time may range from 2 min to 45 min, in particular 3 min to 30 min, 4 min to 20 min, such as approximately 5 min, approximately 10 min or approximately 15 min. In order to accelerate temperature equalization and prevent a non-homogenous distribution of the components of the melt, the melt is preferably mixed during this period.

After reaching a homogenous or essentially homogenous target temperature for release throughout the melt, the melt is released through the die. Extrusion parameters such as diameter and shape of the die, and extrusion pressure will depend on the desired shape and characteristics of the solidified melt, as well as on the characteristics of the melt (depending on the components contained therein), and may be optimized by those skilled in the art. Preferably, the solidified melt is a monophasic mixture of the pharmaceutically active ingredient(s), the polymeric binder, and, optionally, one or more auxiliary agents. In particular, the solidified melt is transparent, bubble-free or essentially bubble-free and essentially or completely free of smears upon visual inspection.

The process of the invention ensures continuous release of melt starting from discontinuous, i.e. batch-wise, preparation of molten pre-dispersion.

Step a) can, for example, be repeated using the same vessel or different vessels in order to obtain multiple batches, e.g., at least two, batches of molten pre-dispersion. These batches are fed into the extruder one after another while extrusion is continued.

When the same vessel is used for preparing each batch of pre-dispersion, a next batch of pre-dispersion can be prepared as soon as the preceding batch of pre-dispersion has been fed into the extruder.

In the solidified melt and in pharmaceutical dosage forms made by further processing the solidified melt, i.e. in delivery systems, the pharmaceutically active ingredient is present as a solid dispersion. A solid dispersion defines a system in a solid state (as opposed to a liquid or gaseous state) comprising at least two components, i.e. pharmaceutically active ingredient and polymeric binder, wherein one component is dispersed evenly throughout the other component or components. For example, the active ingredient is dispersed in a matrix comprised of the polymeric binder. The term solid dispersion encompasses systems having small particles, typically of less than 1 µm in diameter, of one phase dispersed in another phase. When said dispersion of the components is such that the system is chemically and physically uniform or homogeneous throughout or consists of one phase (as defined in thermodynamics), such a solid dispersion will be called a solid solution or a molecular dispersion. Molecular dispersions are preferred physical systems. These systems do not contain any significant amounts of active ingredients in their crystalline or microcrystalline state, as evidenced by thermal analysis (DSC) or X-ray diffraction analysis (WAXS).

Solid dispersions of virtually any desired shape may be formed by forcing the melt through a die of suitable shape, optionally followed by an additional molding or forming step, including injection molding, blow molding, extrusion, or any other molding, forming or casting process known in the art to be suitable for shaping components.

As is understood from the process of the invention which involves melting the polymeric binder, polymeric binders are preferred which can be melted without being decomposed. In this regard, polymeric binders are preferred which can be heated to at least 50 K, e.g. at least 60 K, preferably at least 80 K above the highest glass transition temperature of the polymeric binder (components) without being decomposed. "Without being decomposed" means that the number average molecular weight Mn changes by at most 15%, e.g. at most 10%, preferably, at most 5% when a melt of the polymeric binder is kept for 1 hour at 50 K, 60 K or 80 K above the highest glass transition temperature of the polymeric binder (components).

Preferably, at least one of the active ingredient, the polymeric binder, and the auxiliary agent comprise a component that is semi-solid, tacky or viscous at ambient temperature, e.g., 20° C.

A skilled person is familiar with the meaning of semi-solid, tacky, and viscous.

"Semi-solids" have a thermal transition, e.g. glass transition, close to ambient temperature. Typically, semi-solids show a glass transition temperature below 40° C., for example below 35° C.

The "glass transition temperature" herein refers to the temperature at which a transition from a glassy state into a viscous or rubbery state occurs. This glass transition temperature is suitably determined by Differential Scanning calorimetry (DSC) at a heating rate of 5 K/min. DSC provides a plot of heat flow versus temperature. In the plot of heat flow versus temperature, the glass transition is a gradual transition that occurs over a range of temperatures. At temperatures just below the transition, heat flow is almost constant which results in an almost straight and slowly rising part of the plot. Within the transition, the heat flow increases. The plot is thus steeper but nevertheless typically almost straight in the central part of the transition. A first straight line is fitted to the almost straight and slowly rising part of the plot. A second straight line is fitted to the steeper and almost linear part of the plot in the center of the transition. The glass transition temperature is the temperature at which these straight lines cross each other.

The tack and viscosity of a component, e.g., of a polymer, can be determined by routine measurements known by those skilled in the art.

By "tacky" it is meant that the material has a tack of at least 0.7 Ns at ambient temperature (as measured by a texture analyzer such as TA-XT2i).

By "viscous" it is meant that the material has a dynamic viscosity of 0.2 to 100 Pa·s at ambient temperature.

The polymeric binder may comprise one or more polymeric binder components. When the polymeric binder comprises two or more polymeric binder components, it is generally preferred to use binder components capable of forming a monophasic mixture. A "monophasic mixture" means a polymer blend wherein the polymers are miscible with one another on a molecular chain level and are capable of forming a mixture that is chemically and physically uniform throughout, i.e., forming "one phase".

Most preferably, the polymeric binder comprises a semi-solid polymeric binder component with a glass transition temperature below 40° C., for example below 35° C., and a solid polymeric binder component.

The semi-solid polymeric binder component may, for example, have a glass transition temperature in the temperature range of from −30 to 30° C., preferably, −20 to 20° C., in particular −10 to 10° C.

The glass transition temperature of the solid polymeric binder component is in general above the glass transition temperature of the semi-solid polymeric binder component, e.g., at least 10 K above the glass transition temperature of the semi-solid polymeric binder component.

The solid polymeric binder component may, for example, have a glass transition temperature of 10° C. or higher, preferably 15° C. or higher, in particular 20° C. or higher, e.g., in the range from 10° C. to 110° C., preferably from 15° C. to 90° C., in particular 20° C. to 70° C.

In one aspect according to the invention, the polymeric binder is a non-lipoid carrier substance, e.g. a poly(lactide-co-glycolide). In a particularly preferred aspect according to the invention, the semi-solid polymeric binder component is a poly(lactide-co-glycolide) having a molecular weight distribution centered around a first number average molecular weight $Mn2$ and the solid polymeric binder component is a poly(lactide-co-glycolide) having a molecular weight distribution centered around a first number average molecular weight $Mn1$, wherein $Mn1$ is in the range of from 2000 to 3000 g/mol and the ratio of $Mn1/Mn2$ is from 1.8 to 3.5.

Poly(lactide-co-glycolide) denotes a copolymer (or co-condensate) of lactic acid and glycolic acid. The poly(lactide-co-glycolide) copolymers for use in the present invention are preferably biodegradable, i.e. they degrade in an organism over time by enzymatic or hydrolytic action or by similar mechanisms, thereby producing pharmaceutically acceptable degradation products, and biocompatible, i.e. they do not cause toxic or irritating effects or immunological rejection when brought into contact with a body fluid. The lactic acid units may be L-lactic acid, D-lactic acid or a mixture of both. The proportion of lactic acid units and glycolic acids units within each copolymer may be in the range from 25:75 to 75:25, preferentially in the range from 40:60 to 60:40, in particular 45:55 to 55:45.

The number average molecular weight $Mn1$ is higher than the number average molecular weight $Mn2$. For example, $Mn1$ may be in the range of from 2000 to 3000, in particular 2000 to 2500. A preferred solid polymeric binder component is PLGA Resomer® Mn 2300. The number average molecular weight $Mn2$ may be in the range from 300 to 1200, preferably from 400 to 1000, in particular from 600 to 1000. A preferred semi-solid polymeric binder component is PLGA RESOMER® Mn 800.

"PLGA Resomer® Mn 2300" is available from Evonik and refers to a poly(lactide-co-glycolide), i.e. a copolymer co-condensate of DL-lactic acid and glycolic acid, with proportion of DL-lactic acid units and glycolic acids units being 50:50, and with number average molecular weight Mn=2300. "PLGA Resomer® Mn 800" is also available from Evonik and refers to a poly(lactide-co-glycolide), i.e. a copolymer co-condensate of DL-lactic acid and glycolic acid, with proportion of DL-lactic acid units and glycolic acids units being 50:50, and with number average molecular weight Mn=800.

In a particularly preferred process according to the invention, the semi-solid polymeric binder component is PLGA Resomer® Mn 800 and the solid polymeric binder component is PLGA Resomer® Mn 2300.

Unless defined otherwise or obvious from the context, the molecular weight of polymer is to be understood as the number average molecular weight Mn.

In general, both polymeric binder components, e.g., both poly(lactide-co-glycolides), are monodisperse copolymers. A molecular weight distribution centered around an average value defines the essentially monomodal molecular weight distribution associated with the number average value of each monodisperse copolymer. In general, the polymeric binder components, e.g., the poly(lactide-co-glycolides) have a polydispersity index (which is the quotient of the weight average molecular weight over the number average molecular weight [PDI=Mw/Mn]) of not more than 3.2.

Molecular weights of polymers are measured, for example, by size exclusion chromatography (SEC). Waters HPLC equipment (Waters 515) fitted with 4 coupled Waters Styragel columns as the stationary phase, tetrahydrofuran at 1 mL/min flow rate as the mobile phase, and a Waters 410 refractometer as the detector can be used. Molecular weight can be calculated by the system calibration software using polystyrene standards of known molecular weights.

In general, in the process according to the invention the relative amounts of semi-solid polymeric binder component and solid polymeric binder component can be varied in broad ranges. The polymeric binder components may, for example, be used in a weight ratio of semi-solid polymeric binder component to solid polymeric binder component of 1:20 to 2:1, for example 1:10 to 1.5:1, preferably 1:4 to 1:1. These weight ratios are preferred in particular when the semi-solid polymeric binder component is PLGA Resomer® Mn 800 and the solid polymeric binder component is PLGA Resomer® Mn 2300.

The pre-determined amounts of the different components can be placed in the melting vessel in any desired order. Preferably, at least part of the polymeric binder, e.g., at least part of the semi-solid polymeric binder component, is placed in the melting vessel and is at least partially molten before the active ingredient, and, optionally, the auxiliary agent(s) is (are) placed in the melting vessel. Most preferably, the semi-solid polymeric binder component is placed in the melting vessel and is at least partially molten before the solid polymeric binder component, the active ingredient, and, optionally, the auxiliary agent(s) are placed in the melting vessel.

It is possible to add those components of the pre-dispersion which melt at elevated temperature, e.g., above 20° C., such as, for example, the active ingredient, in the form of particles of any size. The particle size is reduced while the polymeric binder is molten with agitation to disperse the active ingredient in the polymeric binder. A skilled person knows how to adapt agitation such that the mechanical forces are sufficient for breaking even large particles of active ingredient into small pieces.

It is possible to comminute the pharmaceutically active ingredient and/or at least part of the polymeric binder, e.g., the solid polymeric binder component, before it is placed in the melting vessel. This is desired in order to accelerate the formation of the molten pre-dispersion in step a). When at least part of the solid components are placed in the melting vessel in the form of small pieces, i.e. in the form of a comminution product, a uniform molten pre-dispersion will form even more readily.

Every kind of pharmaceutically active ingredient (or combination of pharmaceutically active ingredients) can be used in the process according to the invention.

In one embodiment of the invention, the polymeric binder and the pharmaceutically active ingredient together amount for at least 80 wt-%, such as at least 85 wt-%, or at least 90 wt-%, of the total weight of the pre-dispersion. In another embodiment, the pharmaceutically active ingredient (or combination of pharmaceutically active ingredients) may constitute 1 wt-% to 25 wt-% of the total weight of the solid dispersion product, such as 5 wt-% to 20 wt-%, 10 wt-% to 15 wt-%, or approximately 10 wt-%.

In certain embodiments of the invention, the active ingredient may be selected from nonsteroidal anti-inflammatory agents, steroid anti-inflammatory agents, NMDA antagonists, endothelin receptor antagonists, antioxidants, neurotrophic factors and calcium channel blockers. Examples for nonsteroidal anti-inflammatory agents comprise aspirin, acetaminophen, indomethacin and ibuprofen. Examples for steroid anti-inflammatory agents comprise cortisone, prednisone, prednisolone and dexamethasone. Examples for NMDA antagonists comprise magnesium sulfate and dextromethorphane. Examples for endothelin receptor antagonists comprise clazosentan and bosentan. Examples for antioxidants comprise superoxide dismutase, catalase, nitric oxide, mannitol, allopurinol and dimethyl sulfoxide. Examples for neurotrophic factors comprise endorphins and citicholine. A particularly preferred process of the invention is a process for preparing a solid dispersion product suitable for treating and/or preventing brain vasospasm, such as brain vasospasm associated with traumatic brain injury or subarachnoid hemorrhage. Accordingly, the pharmaceutically active ingredient is a calcium-channel blocking agent, e.g. a calcium-channel blocking agent being effective for treating and/or preventing brain vasospasm, such as brain vasospasm associated with traumatic brain injury or subarachnoid hemorrhage.

Brain vasospasm relates to a temporary or permanent constriction of blood vessels (in particular arteries) located anywhere in the brain. Referring to humans the brain comprises the telencephalon (in particular the cerebral cortex), the diencephalon, the mesencephalon, the metencephalon (in particular the cerebellum) and the myelencephalon. In particular, brain vasospasm relates to a temporary or permanent constriction of blood vessels of the cerebellum and the cerebrum (in particular of the cerebral cortex).

Examples for calcium channel blockers comprise nimodipine, nifedipine, verapamil, nicardipine and isradipine. A particularly preferred active ingredient is selected from nicardipine, a pharmaceutically acceptable salt, hydrate or solvate thereof. The most preferred active ingredient is nicardipine.

One more calcium-channel blocking agent, or one or more active ingredients other than a calcium-channel blocking agent may be used in addition to the calcium-channel blocking agent, e.g., in addition to nicardipine. Pre-determined amount(s) of additional active ingredient(s) may, for example, be placed in the melting vessel in order to obtain a molten pre-dispersion comprising the additional active ingredient(s).

The calcium-channel blocking agent may constitute 1 wt-% to 25 wt-% of the total weight of the solid dispersion product, such as 5 wt-% to 20 wt-%, 10 wt-% to 15 wt-%, or approximately 10 wt-%. In case more than one calcium-channel blocking agent is present, the combined total weight of all calcium-channel blocking agents may constitute 1 wt-% to 25 wt-% of the total weight of the solid dispersion product as described before.

In preferred process of the invention, the semi-solid polymeric binder component is PLGA Resomer® Mn 800 and the solid polymeric binder component is PLGA Resomer® Mn 2300 and the active ingredient is nicardipine, a pharmaceutically acceptable salt, hydrate or solvate thereof. These components are preferably used in a weight ratio of 50 to 80 parts by weight of PLGA Resomer® Mn 2300:27 to 48 parts by weight of PLGA Resomer® Mn 800:9 to 21 parts by weight of nicardipine (calculated as free nicardipine base). For these weight ratios, a suitable second target temperature can easily be determined by those skilled in the art, and may range from 40° C. to 100° C., such as 50° C. to 90° C., in particular 60° C. to 80° C.

The process according to the invention can be carried out using only the polymeric binder and the active ingredient. It is possible to incorporate one or more auxiliary agents into the pre-dispersion, e.g., by placing pre-determined amount(s) of the auxiliary agent(s) in the melting vessel or by adding the auxiliary agent(s) in a later step of the process.

Suitable auxiliary agents are known in the art, and examples thereof comprise antibacterial and antifungal agents, stabilizers, isotonic and pH-controlling agents. The auxiliary agents may be incorporated into the solid dispersion and/or the solid dispersion may be coated with auxiliary agents in order to prevent or delay chemical or physical change during storage (e.g. by penetration of moisture or oxygen) or to preserve the shape of the solid dispersion. The auxiliary agents preferably are biodegradable and biocompatible. Examples for suitable auxiliary agents comprise naturally derived polymers, such as albumin, alginate, cellulose derivatives, collagen, fibrin, gelatin, polysaccharides and artificial polymers such as polyesters (of polylactid acid, polylactic-polyglycolic acid), polyethylene glycol, poloxamers, polyanhydrides and polyoxamers.

The solid dispersion according to the invention is characterized by a particularly high degree of uniformity with regard to its composition, in particular with regard to the distribution of the pharmaceutically active ingredient(s) in the solid dispersion product and with regard to the release of the pharmaceutically active ingredient(s) from the solid dispersion product.

In the process according to the invention, measures common in the art may be taken to avoid a contamination with contaminating organisms or infectious agents (such as eukaryotic cells, bacteria or viruses) or harmful substances (such as chemicals or endotoxins), followed by packaging in sealed containers or the like ensuring avoidance of subsequent contamination.

The solidified melt can be processed further to implants for treating and/or preventing brain vasospasm. This may involve, for example, cutting, shaping and/or sterilizing the solidified melt. For example, sterilization is effected by gamma radiation. The implants may consist of the solid dispersion product.

The implants may have a variety of shapes, such as essentially globular shapes, e.g. balls and ellipsoids, or may have an elongated shape, such as rods or tubes (with a circular cross-section), flattened tubes (with an oval cross-section), triangular, rectangular or polygonal rods or tubes (with essentially triangular, rectangular or polygonal cross-section), wherein the surfaces may have convex or concave forms. The implants may in particular have shapes which mimick the surface topology of the subarachnoid compartment, and may for example have an elongated triangular shape with convex surfaces, thus facilitating their deposition and/or fixation in or on the sulci formed by cerebral gyri, or on the blood vessels in those regions. Implants of desired shape may be formed by injection molding, blow molding, extrusion, or any other molding, forming or casting process known in the art to be suitable for shaping components.

The present invention further relates to a melt extrusion device comprising an extrusion unit, a melting vessel with an opening, an agitating unit, and a displacement element, wherein the agitating unit is arranged such that the content of the melting vessel can be agitated, e.g., stirred, in the melting vessel, and the displacement element is arranged such that it can displace the content from the melting vessel through the opening by reducing the volume of the melting vessel being accessible for the content, and wherein the melting vessel is coupled with the extrusion unit such that the content displaced through the opening enters the extruder unit through a feeding opening of the extruder unit.

The melt extrusion device may further comprise an ultrasound source which is arranged such that the content of the melting vessel can be treated with ultrasound while being agitated.

The invention will now be further illustrated by the following examples, which are not to be construed as a limitation of the present invention.

EXAMPLE 1

PLGA Resomer® Mn 2300 (98.42 g) and PLGA Resomer® Mn 800 (37.49 g) were directly weighed into a mixing and melting beaker at a temperature of 90° C. After approximately ten minutes, the polymers were sufficiently liquid so that the portion of nicardipine base (15.28 g) could be incorporated into the melt. After the nicardipine base had been melted and incorporated by agitation, the pre-dispersion was treated in the beaker with an ultrasonic device at a temperature of 100° C. After 5 minutes of ultrasonic treatment with 20 kHz, the lid was closed and the molten pre-dispersion was transferred with a punch into a twin screw extruder (type: Mini CTW). Extrusion was performed at 68° C., while the temperature of the lid was reduced to 70° C.

After extrusion, the strand was applied on a conveyor belt to adjust the diameter by setting of belt velocity. When the extrudate had reached ambient temperature, segments (length=10 cm) were cut and stored in appropriate vials with desiccant. During extrusion the conveyor belt velocity was adjusted to 70 mm/min (+/−10 mm/min), while the extruder torque was balanced to 15 Ncm (+/−3 Ncm) at a screw speed of 3 rpm. The yield of extrusion was measured to be 78% (118.5 g output of 151.2 g input), mainly due to material losses at the beginning and end of extrusion as well as losses by material transfer of melting container to extruder.

Homogeniety of the contents of the beaker was monitored by routine analysis of samples taken from the beaker before and after agitation and at defined timepoints after start of extrusion. The results are summarized in Table 1

TABLE 1

| Analysis of contents of the beaker | | | |
|---|---|---|---|
| Timepoint | Sample taken from position in beaker | Expected amount of nicardpine [mg] | Measured amount of nicardipine [mg] |
| after melting, before start of agitation | middle | 40 | 43.7 |
| after melting, before start of agitation | edge 1 | 40 | 40.5 |
| after melting, before start of agitation | edge 2 | 40 | 44.5 |

TABLE 1-continued

Analysis of contents of the beaker

| Timepoint | Sample taken from position in beaker | Expected amount of nicardpine [mg] | Measured amount of nicardipine [mg] |
|---|---|---|---|
| after agitation | middle | 40 | 41.7 |
| after agitation | edge 1 | 40 | 43.1 |
| after agitation | edge 2 | 40 | 42.5 |
| start of extrusion | random | 120 | 122.0 |
| after 30 min of extrusion | random | 120 | 122.4 |
| after 60 min of extrusion | random | 120 | 126.0 |
| after 120 min of extrusion | random | 120 | 126.3 |
| after 180 min of extrusion | random | 120 | 122.1 |

Table 1 demonstrates high uniformity of the contents of the beaker throughout the process of the invention.

EXAMPLE 2

One portion of PLGA Resomer® Mn 2300 (37.61 g) was mixed with nicardipine base (15.19 g). A second portion of PLGA Resomer® Mn 2300 was weighed (58.54 g). The mixture of PLGA Resomer® Mn 2300 with nicardipine base and the second portion of PLGA Resomer® Mn 2300 were cryogenically milled as shown in Table 2, i.e. one portion of PLGA Resomer® Mn 2300 was milled separately and the second portion of PLGA Resomer® Mn 2300 was milled with nicardipine base.

TABLE 2

| Cryogenic milling | |
|---|---|
| Precool [min] | 10 |
| Milling cycle [min] | 2 |
| Intermediate cooling time [min] | 2 |
| Number of cycles | 2 |
| Frequency [Hz] | 15 |

The PLGA Resomer® Mn 800 (37.69 g) was directly poured into the melting and mixing beaker until sufficiently liquid by applying 80° C. for 5 minutes. The milled mixture and the milled second portion of PLGA Resomer® Mn 2300 were added to the already molten PLGA Resomer® Mn 800. This mixture was melted at 90° C. for 10 minutes and subsequently homogenized by applying ultrasound for 5 minutes at 20 Hz and 100° C.

Transfer into the extruder and extrusion were carried out as described for example 1.

After extrusion, the strand was applied on a conveyor belt to adjust the diameter by setting of belt velocity. When the extrudate had reached ambient temperature, segments (length=10 cm) were cut and stored in appropriate vials with desiccant. Conveyor belt velocity was 95 mm/min (+/−5 mm/min). Extruder torque was 10 Ncm (+/−3 Ncm). A yield of 86% was reached.

Homogeniety of the contents of the beaker was monitored by routine analysis of samples taken from the beaker before and after agitation and at defined timepoints after start of extrusion. The results are summarized in Table 3

TABLE 3

Analysis of contents of the beaker

| Timepoint | Sample taken form position in beaker | Expected amount of nicardpine [mg] | Measured amount of nicardipine [mg] |
|---|---|---|---|
| after melting, before start of agitation | middle | 40 | 41.1 |
| after melting, before start of agitation | edge 1 | 40 | 40.6 |
| after melting, before start of agitation | edge 2 | 40 | 39.8 |
| after agitation | middle | 40 | 41.1 |
| after agitation | edge 1 | 40 | 40.0 |
| after agitation | edge 2 | 40 | 40.5 |
| start of extrusion | random | 120 | 120.3 |
| after 30 min of extrusion | random | 120 | 120.1 |
| after 60 min of extrusion | random | 120 | 119.8 |
| after 120 min of extrusion | random | 120 | 119.8 |
| after 155 min of extrusion | random | 120 | 119.7 |

Table 3 demonstrates high uniformity of the contents of the beaker throughout the process of the invention.

It is important to note that uniformity of the contents of the beaker in table 1, i.e. without cryo-milling, was fully sufficient for feeding it into an extruder. This demonstrates that it is not necessary to comminute any of the constituents before placing them into the beaker.

The invention claimed is:

1. A melt extrusion process for preparing a solid dispersion comprising a pharmaceutically active ingredient, a polymeric binder, and, optionally, one or more auxiliary agents, comprising
    a) in a batch-wise operation, placing a pre-determined amount of the polymeric binder, a pre-determined amount of the active ingredient, and, optionally, a pre-determined amount of the auxiliary agent(s) in a melting vessel; melting the polymeric binder in the melting vessel with agitation to disperse the active ingredient in the polymeric binder to obtain a molten pre-dispersion;
    b) feeding the pre-dispersion into an extruder to homogenize the pre-dispersion and release a melt through a die; and
    c) allowing the melt to solidify,
    wherein at least one of the active ingredient, the polymeric binder, and the auxiliary agent comprise a component that is semi-solid, tacky or viscous at ambient temperature.

2. The process of claim 1, wherein the polymeric binder and the pharmaceutically active ingredient together amount for at least 80 wt-% of the total weight of the pre-dispersion.

3. The process according to claim 1, wherein the polymeric binder comprises a semi-solid polymeric binder component with a glass transition temperature below 40° C. and a solid polymeric binder component.

4. The process according to claim 3, wherein the solid polymeric binder component has a glass transition temperature of 10° C. or higher.

5. The process according to claim 3, wherein the semi-solid polymeric binder component is a poly(lactide-co-glycolide) having a molecular weight distribution centered around a number average molecular weight Mn2 and the solid polymeric binder component is a poly(lactide-co-glycolide) having a molecular weight distribution centered around a number average molecular weight Mn1, wherein Mn1 is in the range of from 2000 to 3000 g/mol and the ratio of Mn1/Mn2 is from 1.8 to 3.5.

6. The process according to claim 3, wherein the weight ratio of semi-solid polymeric binder component to solid polymeric binder component is from 1:10 to 1.5:1.

7. The process according to claim 1, wherein the active ingredient is selected from nicardipine, a pharmaceutically acceptable salt, hydrate or solvate thereof.

8. The process according to claim 1, wherein at least part of the polymeric binder is placed in the melting vessel and is at least partially molten before the active ingredient, and, optionally, the auxiliary agent(s) is (are) placed in the melting vessel.

9. The process according to claim 1, wherein an ultrasonic treatment is carried out while dispersing the active ingredient in the polymeric binder and/or after dispersing the active ingredient in the polymeric binder.

10. The process according to claim 1, wherein the temperature of the pre-dispersion while being fed into the extruder is above its solidification temperature.

11. The process according to claim 1, wherein feeding the pre-dispersion into the extruder involves a displacement of the pre-dispersion from the melting vessel through an opening of the melting vessel, the displacement of the pre-dispersion being enforced by reducing a volume of the melting vessel being accessible for the pre-dispersion.

12. The process according to claim 11, wherein the volume of the melting vessel being accessible for the pre-dispersion is reduced by a translational movement of a displacement element, e.g., a punch, into the melting vessel.

13. The process according to claim 1, wherein the pharmaceutically active ingredient and/or at least part of the polymeric binder is comminuted before it is placed in the melting vessel.

* * * * *